United States Patent
Argade

(10) Patent No.: US 7,459,301 B2
(45) Date of Patent: Dec. 2, 2008

(54) STEREOISOMERICALLY ENRICHED N-PROTECTED β-LACTAMS USING CANDIDA ANTARCTICA

(75) Inventor: Ankush Argade, Foster City, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 399 days.

(21) Appl. No.: 11/281,186

(22) Filed: Nov. 15, 2005

(65) Prior Publication Data

US 2006/0166308 A1  Jul. 27, 2006

Related U.S. Application Data

(60) Provisional application No. 60/628,401, filed on Nov. 15, 2004.

(51) Int. Cl.
*C12P 41/00* (2006.01)

(52) U.S. Cl. ..................................................... 435/280

(58) Field of Classification Search ................. None
See application file for complete search history.

(56) References Cited

U.S. PATENT DOCUMENTS 6,780,634 B1  8/2004  Bernegger-Egli

FOREIGN PATENT DOCUMENTS

WO  WO 00/03032 A1  1/2000

OTHER PUBLICATIONS

Forro et al., "Lipase-Catalyzed Enantioselective Ring Opening of Unactivated Alicyclic-Fused beta Lactams in an Organic Solvent", Organic Letters 5 (8) : 1209-1212 (2003), and supporting information.*
Supporting information for Forro et al, pp. 1-7 (2003).*
International Search Report from PCT/US05/041276, Jul. 12, 2006.
Forro et al., 2004, Direct and Indirect Enzymatic Methods for the Preparation of Enantiopure Cyclic β-Amino Acids and Derivatives from β-Lactams, *Mini-Reviews in Organic Chemistry*, 1(1):93-102.
Adam et al., 2000, "Synthesis of Optically Active α-Methylene β-Lactams through Lipase-Catalyzed Kinetic Resolution," *Journal of Organic Chemistry*, 65(16):4919-4922.
Forro et al., "Vapour-assisted enzymatic hydrolysis of β-lactams in a solvent-free system," Tetrahedron: Asymmetry, 19:1005-1009 (2008).

* cited by examiner

*Primary Examiner*—Sandra E. Saucier
(74) *Attorney, Agent, or Firm*—McDonnell Boehnen Hulbert & Berghoff LLP

(57) ABSTRACT

The present disclosure provides enzymatic methods for generating stereoisomerically pure products by resolving a racemic mixture of N-protected β-lactams with a lipase from *Candida antarctica* with high stereospecificity. The presence of a carbamate protecting group, such as the tert-butoxycarbonyl group protecting group, on the β-lactam enhances enzyme catalysis and stereoselectivity.

13 Claims, No Drawings

STEREOISOMERICALLY ENRICHED N-PROTECTED β-LACTAMS USING CANDIDA ANTARCTICA

1. CROSS-REFERENCE TO RELATED APPLICATION

This application claims benefit under 35 U.S.C. § 119(e) to application Ser. No. 60/628,401, filed Nov. 15, 2004, the contents of which is incorporated herein by reference.

2. FIELD

The present disclosure relates to methods for generating stereospecific products from a racemic mixture of N-protected β-lactams that can be used for chiral syntheses. In particular, the method can be used to synthesize stereoisomerically pure β-lactam and β-amino carboxylic acid compounds that can be used as starting materials to synthesize a wide variety of stereoisomerically pure compounds.

3. BACKGROUND

The use of enzymes in organic syntheses has become prevalent. By exploiting the tools that nature provides, chiral molecules can be selectively separated or resolved, or chirality can be infused into a molecule having no chirality, by virtue of the enzyme's own chiral nature. Enzymes provide precise stereocontrol and accelerate chemical transformations that are otherwise difficult to carry out using conventional synthetic chemistry. More importantly, enzymes generally obviate the need for protecting group manipulations frequently hampering and adding additional steps in a chemical synthesis. As such, enzymes are commercially used to synthesize and/or resolve active pharmaceuticals and useful intermediates leading thereto.

Many carbon based pharmaceuticals as well as intermediates have chiral centers which permit multiple stereoisomers or antipodes. Typically, each stereoisomer has distinct chemical and physical properties. Some of those properties can be fatal and some can be pharmaceutically useful. For example, (S)-thalidomide can cause severe birth defects, while (R)-thalidomide is a safe and effective sedative, and a treatment for diseases such as cancer. These dramatic differences have led the Food and Drug Administration to require each enantiomer of a racemic drug to be put through clinical testing individually prior to receiving approval for widespread distribution. Thus, there is a need for stereoselective methods for synthesizing or enriching stereoisomers. In particular, there exists a need for biocatalytic process for synthesizing enantiomeric or diastereomerically pure pharmaceutical and intermediates.

4. SUMMARY

The present disclosure provides methods for generating stereospecific products from a racemic mixture of N-protected β-lactams that can be used for chiral synthesis. The method can be used to synthesize stereoisomerically pure β-lactam and β-amino carboxylic acid derivatives that can be used as starting materials to synthesize specific diastereomers of a wide variety of molecules. For example, the stereoisomerically pure β-lactam can be used as a starting material to synthesize diastereomerically pure antiproliferative (1R,2R,3S,4S)-N-4-(3-aminocarbonyl-bicyclo[2.2.1]hept-5-ene-2-yl)-5-fluoro-N2-[3-methyl-4-(4-methylpiperazin-1-yl)phenyl]-2, 4-pyrimidinediamine, and the various compounds described in copending application Ser. No. 11/133,419 filed May 18, 2005, international application no. PCT/USO5/17470 and application Ser. No. 11/280,066 entitled "Stereoisomerically Enriched 3-Aminocarbonyl Bicycloheptene Pyrimidinediamine Compounds and Their Uses," filed concurrently herewith.

The method generally comprises contacting a (2-exo, 3-exo) cis β-lactam comprising a mixture of enantiomers according to structural formulae 1 and 2:

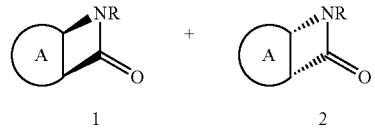

wherein A represents a saturated or unsaturated, monocyclic, polycyclic or bridged polycyclic ring and R represents a protecting group, with a lipase from *Candida antarctica* to yield stereoisomerically pure products according to structural formulae 1 and 4:

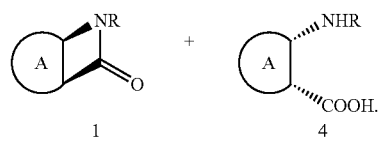

Examples of ring A include, but are not limited to, bicycloheptenyl, bicycloheptyl, cyclohexyl, cyclohexenyl, cyclopentyl, cyclopentenyl, cyclopropyl, cyclobutyl, and the like.

Ring A can be substituted at one or more carbon atoms, or optionally interrupted by, a combination of one or more alkyl, alkanyl, alkenyl, alkynyl, alkylidiyl, alkylene, cycloalkyl, aryl, halogen, haloalkyl, hydroxalkyl, thiols, amines, hydroxyls, ethers, alkoxy, C=O, S=O, P=O, nitro, cyano, Se=O and/or N=O groups.

Suitable protecting groups R have the formula —C(X)YR$^1$, where X is O or S; Y is O or S; and R$^1$ is selected from unsubstituted or substituted lower alkyl, unsubstituted or substituted lower alkanyl, unsubstituted or substituted (C6-C14) aryl and unsubstituted or substituted (C7-C20) arylalkyl. Thus, protecting group R, taken together with the β-lactam nitrogen to which it is bonded, forms a carbamate or a carbamate equivalent, such as a thiocarbamate. In some embodiments, R$^1$ is selected from t-butyl, benzyl and fluoren-9-yl.

In some embodiments, the β-lactam is protected as a carbamate such that protecting group R is of the formula —C(O)OR$^1$, where R$^1$ is as previously defined. In some embodiments, R$^1$ is selected from unsubstituted lower alkyl or alkanyl, unsubstituted or substituted mono-, bi- or tricyclic (C6-C14) aryl and unsubstituted (C7-C20) arylalkyl. Specific, non-limiting examples of exemplary carbamate protecting groups R include tert-butoxycarbonyl (Boc), benzyloxycarbonyl and 9-fluorenylmethoxycarbonyl.

Lipases derived from *Candida antarctica* are commercially available in different forms such as resin-immobilized, lyophilized or suspended preparations. All of these lipases can be used in the methods described herein. For ease of handling, immobilized lipases are advantageous. Furthermore, although, resolution of N-protected racemic β-lactam works with stoichiometric or excess amounts of enzyme, only a catalytic amount of the enzyme is needed.

The resolution of N-protected racemic β-lactam can proceed in various solvents, including but not limited to, diisopropyl ether, butanol, tetrahydrofuran, toluene, hexanes and mixtures of such solvents. Typically, for more efficient conversion, the reaction solvent(s) contains a catalytic amount of water, for example, in the range of about 0.1-1.0%. The necessary amount of water can be achieved by using commercially available anhydrous solvents without further purification or distillation.

Another variable that affects the enzyme-mediated resolution of racemates is temperature. The temperature can be varied and modulated to accelerate or decelerate the resolution process. In general, the enzymatic resolution of racemates can proceed at a temperature in the range of about 0-80° C., or more specifically in the range of about 20-60° C.

5. DETAILED DESCRIPTION

5.1 Definitions

As used herein, the following terms are intended to have the following meanings:

"Alkyl" by itself or as part of another substituent refers to a saturated or unsaturated branched, straight chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl propan-2-yl, cyclobutan-1-yl, but-1-en-1-yl, but-1-en-2-yl, 2-methyl prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to an alkyl group containing from 1 to 6 carbon atoms.

"Alkanyl" by itself or as part of another substituent refers to a saturated branched, straight chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec butyl), 2-methyl propan-1-yl (isobutyl), 2-methyl propan-2-yl (t-butyl), cyclobutan-1-yl, etc.; and the like.

"Alkenyl" by itself or as part of another substituent refers to an unsaturated branched, straight chain or cyclic alkyl having at least one carbon carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-2-en-1-yl, 2-methyl prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight chain or cyclic alkyl having at least one carbon carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but 3-yn-1-yl, etc.; and the like.

"Alkyldiyl" by itself or as part of another substituent refers to a saturated or unsaturated, branched, straight chain or cyclic divalent hydrocarbon group having the stated number of carbon atoms (i.e., C1 C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan 1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1, 1-diyl, 2-methanylidene propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group containing 1 to 6 carbon atoms. In some embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1, 4-diyl (butano); and the like (also referred to as alkylenes, defined infra).

"Alkylene" by itself or as part of another substituent refers to a straight chain saturated or unsaturated alkyldiyl group having two terminal monovalent radical centers derived by the removal of one hydrogen atom from each of the two terminal carbon atoms of straight chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is (C1-C6) or (C1-C3) alkylene. In some embodiments, the alkylene group is a straight chain saturated alkano group, e.g., methano, ethano, propano, butano, and the like.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cycloheptyls such as cycloheptanyl and cycloheptenyl; cyclohexyls such as cyclohexanyl and cyclohexenyl; cycloheptyls such as cycloheptanyl and cycloheptenyl; and the like.

"Aryl" by itself or as part of another substituent refers to a monovalent aromatic hydrocarbon group having the stated number of carbon atoms (i.e., C6-C14 means from 6 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as indacene, s indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is (C6 C10). Specific examples are phenyl and naphthyl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

The above defined groups may include prefixes and/or suffixes that are commonly used in the art to create additional well recognized substituent groups. As examples, "alkyloxy" or "alkoxy" refers to a group of the formula —OR', "alkylamine" refers to a group of the formula —NHR' and "dialkylamine" refers to a group of the formula —NR'R', where each R' is independently an alkyl. As another example, "haloalkoxy" or "haloalkyloxy" refers to a group of the formula —OR", where R" is a haloalkyl.

5.2 Resolution of Stereoisomerically Pure β-Lactams Using *Candida Antarctica*

In one aspect, a method is provided for resolving mixtures of β-lactam diastereomers and/or enantiomers, such as racemic mixtures of (2-exo, 3-exo) cis β-lactams, into stereoisomerically pure products using a lipase enzyme from *Candida antarctica*. In some embodiments, the method comprises contacting a (2-exo, 3-exo) cis N-protected β-lactam comprising a mixture of enantiomers according to structural formulae 1 and 2:

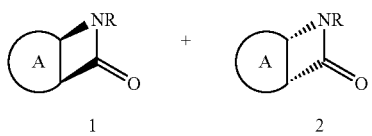

with a lipase from *Candida antarctica*, wherein A represents a saturated or unsaturated, monocyclic, polycyclic or bridged polycyclic ring and R represents a protecting group.

The A ring can be substituted at one or more carbon atoms, or interrupted by, a combination of one or more alkyl, alkanyl, alkenyl, alkynyl, alkylidiyl, alkylene, cycloalkyl, aryl, halogen, haloalkyl, hydroxalkyl, thiols, amines, hydroxyls, ethers, alkoxy, C=O, S=O, P=O, nitro, cyano, Se=O and/or N=O groups. Examples of A rings include, but are not limited to, bicycloheptenyl, bicycloheptyl, cyclohexyl, cyclohexenyl, cyclopentyl, cyclopentenyl, cyclopropyl, and the like.

Suitable protecting groups R have the formula —C(X)YR$^1$, where, X is O or S; Y is or S; and R$^1$ is selected from unsubstituted or substituted lower alkyl, unsubstituted or substituted lower alkanyl, unsubstituted or substituted (C6-C14) aryl and unsubstituted or substituted (C7-C20) arylalkyl. Thus, protecting group R, taken together with the β-lactam nitrogen to which it is bonded, forms a carbamate or a carbamate equivalent, such as a thiocarbamate. In some embodiments, R$^1$ is selected from t-butyl, benzyl and fluoren-9-yl.

In some embodiments, the β-lactam is protected as a carbamate such that protecting group R is of the formula —C(O)OR$^1$, where R$^1$ is as previously defined. In some embodiments, R$^1$ is selected from unsubstituted lower alkyl or alkanyl, unsubstituted or substituted mono-, bi- or tricyclic (C6-C14) aryl and unsubstituted (C7-C20) arylalkyl. Specific, non-limiting examples of exemplary carbamate protecting groups R include tert-butoxycarbonyl (Boc), benzyloxycarbonyl and 9-fluorenylmethoxycarbonyl.

The importance of the carbamate protecting group, or its equivalent, in the enzymatic resolution of racemic β-lactams is apparent from the discussion below.

In general, lipases are enzymes that catalyze the hydrolysis of fats into fatty acids and glycerol. In addition to resolving esters (see, e.g., Kurokawa et al., 2004, Bull. Chem. Soc. Jpn 77:1021-1025), it has been reported that some lipases from *Candida antarctica* resolve racemic β-lactams that are either unprotected at the β-lactam amide nitrogen atom (via opening of the lactam ring), or that are protected at this nitrogen atom with an N-acyloxymethyl ester protecting group (via hydrolysis of the remote ester group) (see, Forró et al., 2004, Mini-Review in Organic Chemistry 1:93-102). The aforementioned enzymatic resolution of unprotected β-lactams, although providing products of high enantiomeric excess, suffers from poor yields and necessitate use of a full equivalent of water. The methods using N-acyloxymethyl ester protected lactams suffer from poor yields and low enantiomeric excess.

N-Benzoyl protected β-lactams have been enzymatically resolved using various enzymes, but not *Candida antarctica* (see Brieva et al., 1993, J. Org. Chem. 58(5):1068-1075). The benzoyl protected β-lactams were found to be unstable in aqueous media, undergoing hydrolysis without enzyme participation, presumably due to over-activation by the benzoyl group. Even so, when using organic media for the resolutions, good enantiomeric excess was achieved, however with poor yields.

In contrast, the inventors of the present application have discovered that the use of β-lactams in which the amide ring nitrogen atom is protected as a carbamate enhance reactions with lipases from *Candida antarctica* and provide stereoisomerically pure products in high yields. While not intending to be bound by any theory of operation, it is believed that the carbamate activates the β-lactam toward lipase catalysis, but not to the point of instability in aqueous media. It is believed that carbamate equivalents as described herein will also activate the β-lactam toward lipase catalysis without aqueous instability. This combination of enhanced reactivity and relative stability in aqueous media of the N-protected β-lactam, along with lipases from *Candida antarctica* provide novel means for producing stereoisomerically pure products in high yields.

Lipases from *Candida antarctica* are commercially available in variety of different forms and preparations, including resin-immobilized, lyophilized and suspended preparations, from, for example BioCatalytics (Pasadena, Calif., USA), Novozyme (Franklinton, N.C., USA,), Sigma (St. Louis, Mo., USA) and Aldrich Chemical Co. (Milwaukee, Wis., USA). As a specific example, suitable lipases from *Candida antarctica* are sold under the tradename Chirazyme by Roche Diagnostics Corp. (Indianapolis, Ind.). Although lyophilized and suspended preparations are useful in the methods described herein, the use of immobilized enzymes provides several advantages, including, but not limited to, improved enzyme stability, convenience of handling and ease with which the enzyme can be recycled. As a non-limiting example, Table 1 lists some of the lipases from *Candida antarctica* that are commercially available through BioCatalytics (Pasadena, Calif., USA) that are suitable for use in the methods described herein.

TABLE 1

| Catalog No. | Product Description |
| --- | --- |
| IMB-101 | Lipase from *Candida antarctica*, type B, carrier-fixed 1 (equivalent to Chirazyme L2, c-f) |
| IMB-102 | Lipase from *Candida antarctica*, type B, carrier-fixed 2 (equivalent to Chirazyme L2, C2) |
| IMB-103 | Lipase from *Candida antarctica*, type B, carrier-fixed 3 (equivalent to Chirazyme L2, C3) |
| IMB-104 | Lipase from *Candida antarctica*, type A, carrier-fixed 1 (equivalent to Chirazyme L5, c-f) |

Generally, each lipase enzyme exhibits some degree of unique thermostability, substrate specificity and/or chemo-specificity. In some embodiments, lipases from *Candida antarctica* type B are used.

In some embodiments, a resin-immobilized lipase from *Candida antarctica* is used. When protected with a Boc group at the lactam amide nitrogen, it has been observed that the enzyme selectively binds and hydrolyzes the enantiomer of structural formula 2 with high specificity, but does not react with the enantiomer of structural formula 1. While not intending to be bound by any theory of operation, it is believed that the carbamate group activates the enzymatic resolution process. Moreover, the carbamate group, by virtue of its relative lipophilicity, aids in the separation of the resultant diastereomeric products, providing stereoisomerically pure products in high yields. It is expected that protecting groups other than Boc that have similar properties, and groups that are equivalent to carbamates as described herein, will yield similar results.

Suitable carbamates include, but are not limited to, those described above, including Boc, benzyloxycarbonyl and 9-fluorenylmethoxycarbonyl. Other useful carbamates can be found in Greene & Wuts., *Protective Groups in Organic Synthesis*, 3rd Ed., John Wiley & Sons, Inc., New York (1999) and the references cited therein (see, e.g., the myriad carbamates at pp. 503-550, the disclosure of which is incorporated herein by reference.) Any carbamate protecting groups in a β-lactam that can be cleaved without racemization of the chiral stereocenters in a stereoisomerically pure compound are useful.

In general, the method for generating stereoisomerically pure compounds comprises contacting an N-protected β-lactam comprising a mixture of enantiomers according to structural formulae 1 and 2 (for example, a racemic mixture) with a lipase enzyme from *Candida antarctica* in a reaction solvent. As mentioned above, the enzyme hydrolyzes one stereoisomer, but leaves the other stereoisomer intact. The amount of enzyme used is not critical and can be varied. Usually, a catalytic amount of enzyme is sufficient. In other situations, at least one molecule of enzyme per 500 molecules of substrate is desirous to achieve adequate resolution of N-protected β-lactams.

Similarly, the choice of reaction solvent can be varied, depending, in part, on the solubility of the starting materials and products. Examples of common solvents useful for the methods described herein include diisopropyl ether, tetrahydrofuran, butanol, hexanes, toluene and acetonitrile. Mixtures of these solvents may also be used. The use of organic solvents for enzymatic resolutions, rather than aqueous systems, is particularly useful. Since some water may be necessary to adequately hydrate the enzyme, a catalytic amount of water, for example, in the range of about 0.1-1.0% is advantageous. The catalytic amount of water can usually be achieved by using fresh commercially available anhydrous solvents without further distillation, as these solvents typically are not 100% water free. For a discussion of the importance and use of water in enzymatic reactions carried out in organic solvents, see Klibanov, 1997, "Why Are Enzymes Less Active In Organic Solvents Then In Water?" Trends in Biotechnology 15(3): 97-101, the disclosure of which is incorporated herein by reference.

Temperature also governs the reactivity and stereoselectivity of the enzyme. Generally, enzymes are susceptible to temperature. For practical applications, the stereoselective methods described herein can be carried out at a temperature in the range of about 0-80° C. In some embodiments it may be advantageous to use a temperature in the range of about 20-60° C. The optimum temperature for carrying out any particular stereoselective reaction described herein can be determined by the skilled artisan by, for example, monitoring the progress of the reaction using analytical techniques such as, but not limited to, nuclear magnetic resonance, mass spectrometry, IR spectroscopy, UV/VIS absorption, optical polarimetry, GC chromatography, HPLC, or combinations thereof, over time.

5.3 Uses for Stereoisomerically Enriched β-Lactams

As mentioned above, lipases from *Candida antarctica* selectively hydrolyze the enantiomer of structural formula 2, leaving the enantiomer of structural formula 1 intact. Hence, the product of the reaction is a mixture of compounds according to structural formulae 1 and 4:

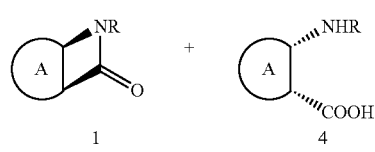

wherein A and R are as previously defined.

If desired, β-lactam 1 and N-protected β-amino carboxylic acid 4 can be isolated and/or purified using standard analytic techniques known to the skilled artisan, such as, but not limited to, electrophoresis, selective precipitation, fractional crystallization, ion exchange chromatography, high pressure liquid chromatography (HPLC), or distillation. In some embodiments, β-lactam 1 can be isolated from amino carboxylic acid 4 by converting one product to a water soluble form, for example a carboxylate salt, and separating the products based on their respective solubilities in aqueous and organic solvents. Specific examples of such separations are provided in the Examples sections.

Stereoisomerically pure β-lactam 1 and N-protected β-amino carboxylic acid 4 are both useful as starting materials to synthesize specific diastereomers of a wide variety of molecules. For example, stereoisomerically pure β-lactam 1 can be used as a starting material to synthesize diastereomerically pure antiproliferative (1R,2R,3S,4S)-N-4-(3-aminocarbonylbicyclo[2.2.1]hept-5-en-2-yl)-5-fluoro-N-2-[3-methyl-4-(4-methylpiperazin-1-yl)phenyl]-2,4-pyrimidinediamine. An exemplary embodiment of the synthesis of this compound is illustrated in Scheme (I). In the various exemplary reaction schemes discussed herein illustrated with 3-aminocarbonylbicyclo[2.2.1]hept-5-en-2-yl-2,4-pyrimidinediamine compounds, including Scheme (I), compound numbers followed by a suffix, such as a, b, r1 and r2, refer to specific diastereomers and racemates, as follows:

a=(1R,2R,3S,4S)

b=(1S,2S,3R,4R)

r1=2-exo-3-exo cis r2=2-endo-3-endo cis

26b. Treatment of β-lactam 16a with aqueous ammonium hydroxide gives N-Boc-amino carboxamide derivative 28a, which is soluble in organic solution, and salt 27b, which is soluble in aqueous solution. N-Boc-amino carboxamide derivative 28a can be partitioned into organic solution. Deprotection of the Boc group with TFA yields amino carboxamide 30a, which can now undergo a nucleophilic aromatic substitution reaction with 5-fluoro-2,4-dichloro-pyrimidine 34 to yield compound 36a. Nucleophilic aromatic substitution of compound 36a with aniline 7 yields diastereomerically pure (1R,2R, 3S, 4S)-N-4-(3-aminocarbonyl-bicyclo[2.2.1]hept-5-en-2-yl)-5-fluoro-N-2-[3-methyl-4-(4-methylpiperazin-1-yl)phenyl]-2,4-pyrimidinediamine 60a. Those of skill in the art will appreciate that the stereoisomeric configuration and optical purity of stereisomer 16a will, in most circumstances, determine the stereoisomeric configuration and optical purity of (1R,2R, 3S, 4S)-N-4-(3-aminocarbonyl-bicyclo[2.2.1]hept-5-en-2-yl)-5-fluoro-N-2-[3-methyl-4-(4-methylpiperazin-1-yl)phenyl]-2,4-pyrimidinediamine 60a.

Additional 3-substituted-cycloalkyl-2,4-pyrimidinediamine compounds that can be synthesized utilizing stereoisomerically pure β-lactam 1 as a starting material are described in copending application Ser. No. 11/133,419 filed May 18, 2005, international application no. PCT/US05/17470 and application Ser. No. 11/280,066 entitled "Stereoisomerically Enriched 3-Aminocarbonyl Bicycloheptene Pyrimidinediamine Compounds and Their Uses," filed concurrently herewith, the disclosures of which are incorporated herein by reference.

6. EXAMPLES

The inventions described herein are further defined by reference to the following examples, which describe the preparation of various compounds described herein, methods

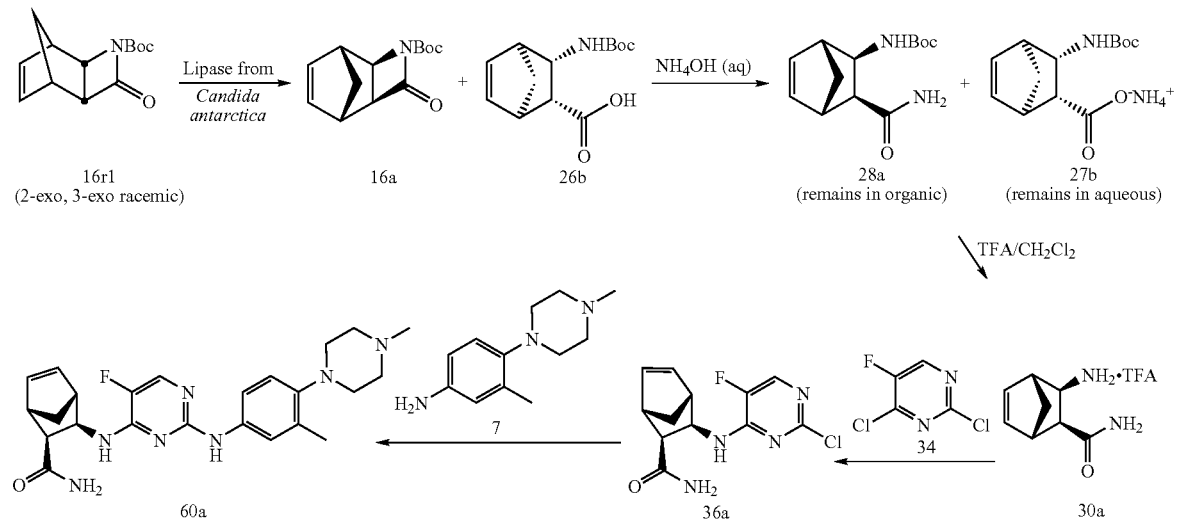

Scheme (I)

Referring to Scheme (I), the enzymatic resolution of a racemic mixture of (2-exo, 3-exo) cis N-Boc protected β-lactam 16r1, which comprises stereoisomers 16a and 16b (not illustrated) using a lipase from *Candida antarctica* yields β-lactam 16a and N-Boc β-amino carboxylic acid derivative for assaying their biological activity, and methods for their use. It will be apparent to one of ordinary skill in the art that many modifications, both to the materials and methods, may be practiced without departing from the scope of the invention.

6.1 Preparation of 3-Aza-4-oxo-tricyclo[4.2.1.0(2,5)]non-7-ene

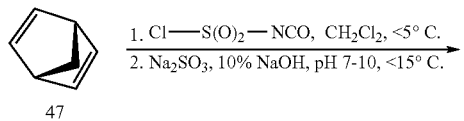

47

1. Cl—S(O)₂—NCO, CH₂Cl₂, <5° C.
2. Na₂SO₃, 10% NaOH, pH 7-10, <15° C.

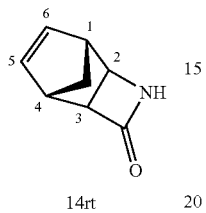

14rt
(racemic, 2-exo-3-exo)

Procedure: Part 1: A solution of 2,5-norbornadiene 47 (25.0 mL, 0.246 mole) in CH₂Cl₂ (110 mL, fresh bottle) was cooled in an ice/NaCl bath (−10° C.). To this was added drop-wise a solution of CSI (21.4 mL, 0.246 mole) in CH₂Cl₂ (45 mL, fresh bottle) at a rate to maintain the temperature below 5° C. (the addition took approx. 1.25 hr.). Upon completion of the addition, the reaction mixture was stirred for 1 hour at 0-5° C. and then removed from the cooling bath and allowed to warm to 20° C. The reaction mixture was quenched with water (60 mL) and vigorously stirred for several minutes. The organic layer was separated, washed with brine, and dried with Na₂SO₄. Concentration gave a light brown oil.

Part 2: A mixture of Na₂SO₃ (24.5 g), water (70 mL), and CH₂Cl₂ (30 mL) was cooled in an ice/NaCl bath. The oil from Part 1 was diluted to 100 mL with CH₂Cl₂ and added drop-wise to the above mixture at a rate to maintain the temperature below 15° C. (the addition took approx. 1.75 hr). The pH of the reaction mixture was monitored with a pH meter and kept basic (pH 7-10) by adjusting with 10% NaOH (w/v) (as needed). Upon completion of the addition, the reaction mixture was stirred for 1 hour at 5-10° C. (final pH was 8.5). The reaction mixture was poured into a separatory funnel and the CH₂Cl₂ layer separated. This organic phase was a thick and gelatinous solid suspension. It was diluted with water (approx. 400 mL) to make a more free flowing solution. The aqueous layer was further extracted with CH₂Cl₂ (4×100 mL). (Alternatively, the solids can be separated from the CH₂Cl₂ by centrifugation. The solids can then be diluted with water (until almost all dissolved) and extracted with CH₂Cl₂). The aqueous layer was further extracted with CH₂Cl₂ (10× 100 mL). The CH₂Cl₂ extracts were monitored by TLC for the presence of product. The combined organic extracts were washed with brine, dried with MgSO₄, and filtered through diatomaceous earth (celite). Removal of solvent gave the desired product, racemic-2-exo-3-endo 3-aza-4-oxo-tricyclo [4.2.1.0(2,5)]non-7-ene 14r1 as white solid (20.5 g, 62%). ¹H NMR (DMSO-d₆): δ 8.01 (bs, 1H), 6.22 (dd, J=3.3 and 5.4 Hz, 1H), 6.12 (dd, J=3.3 and 5.4 Hz, 1H), 2.88 (dd, J=1.5 and 3.3, 1H), 2.79 (bs, 1H), 2.74 (bs, 1H), 1.58 (d, J=9.3 Hz, 1H), and 1.47 (d, J=9.3 Hz, 1H).

6.2 Preparation of 4-Oxo-3-tert-butoxycarbonylaza-tricyclo[4.2.1.0(2,5)]non-7-ene

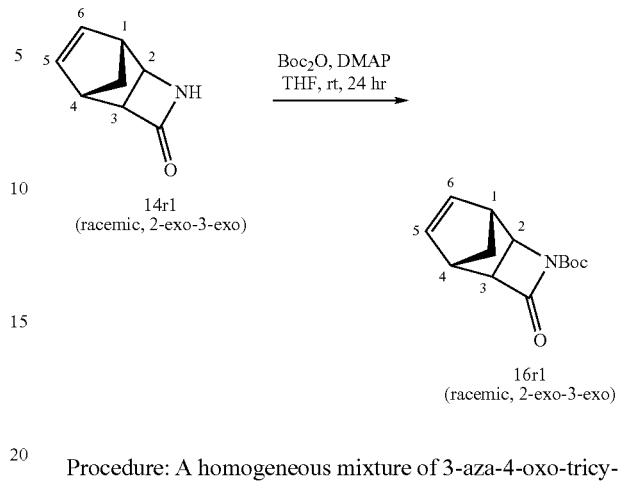

Procedure: A homogeneous mixture of 3-aza-4-oxo-tricyclo[4.2.1.0(2,5)]non-7-ene (14r1; racemic-2-exo-3-exo; 10.0 g, 74 mmol), (Boc)₂O (16.1 g, 74 mmol) and DMAP (1.1 g) in CH₂Cl₂ was stirred under N₂ at room temperature for 24 hours. To this reaction mixture were added EtOAc (100 mL) followed by H₂O (100 mL) and stirred for additional 1 hour. The organic layer was separated and washed with H₂O (2×100 mL). The organic layer was dried over anhydrous Na₂SO₄ and solvent was removed under a reduced pressure to afford 4-oxo-3-tert-butoxycarbonylaza-tricyclo[4.2.1.0(2,5)]non-7-ene (16r1; racemic-2-exo-3-exo) (16.5 g, 70%); ¹H NMR (DMSO-d₆): δ 6.29 (dd, J=3.3 and 5.4 Hz, 1H), 6.19 (dd, J=3.3 and 5.4 Hz, 1H), 3.77 (d, J=4.5 Hz, 1H), 3.13 (bs, 1H), 3.08-3.04 (m, 1H), 2.93 (bs, 1H), 1.45 (s, 9H). LCMS: 95%

6.3 Enzymatic Preparation of Stereoisomerically Pure (1R,2R,3S,4S)-N-4-(3-Aminocarbonylbicyclo [2.2.1]hept-5-en-2-yl)-5-fluoro-N-2-[3-methyl-4-(4-methylpiperazin-1-yl)phenyl]-2,4-pyrimidinediamine Using Chirazyme

6.3.1 Preparation of Stereochemically Pure N-Boc-β-Lactam

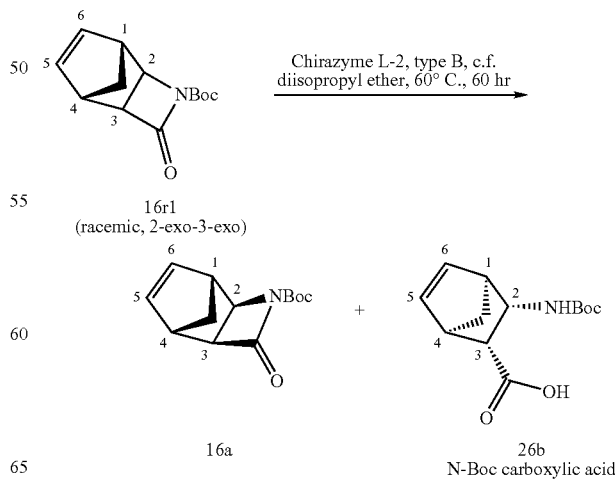

Procedure: A dry sealed tube charged with 4-oxo-3-tert-butoxycarbonylaza-tricyclo[4.2.1.0(2,5)]non-7-ene (16r1; racemic-2-exo-3-exo) (4.0 g, 17.02 mmol), resin bound/immobilized chirazyme L-2, type B, c.f. (8.0 g, purchased from BioCatalytics Inc., Pasadena, Calif.) and diisopropyl ether (80 mL) was gently shaken in an incubator at 60° C. for 60 hours. (The enzymatic resolution of racemic N-Boc β-lactam 16r1 was followed by proton NMR. The integration of tert-butyl group of enantiomerically pure N-Boc lactam 16a and N-Boc carboxylic acid 26b was seen in 1:1 ratio). The resulting reaction mixture was filtered and the solid resin was washed with diisopropyl ether (2×40 mL). The filtrate was concentrated to afford a mixture of enatiomerically pure N-Boc-β-lactam 16a and N-Boc carboxylic acid 26b (total mass: 4.0 gm).

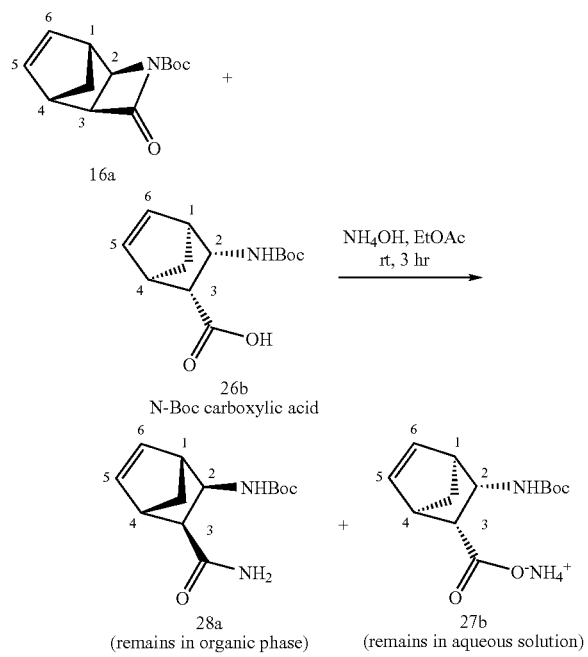

Procedure: A round bottom equipped with a rubber septum and a magnetic stirring bar was charged with a mixture of enantiomerically pure N-Boc-lactam 16a and N-Boc carboxylic acid 26b (4.0 g) under a positive pressure of nitrogen. To this were added ethyl acetate (50 mL) followed by 25% aqueous ammonium hydroxide (50 mL) and stirred at room temperature for 3 hours. The reaction progress was monitored by TLC. The ethyl acetate layer was separated and washed with 5% aqueous solution of $NaHCO_3$ (40 mL), dried over anhydrous $Na_2SO_4$ and solvent was evaporated to afford 2.00 gm (7.93 mmol out of a theoretical 8.51 mmol; 93% yield) of the desired enantiomerically pure N-Boc carboxamide 28a with greater than 99% enantiomeric excess, as determined by chiral HPLC. The aqueous solution containing the N-Boc ammonium carboxylate 27b upon acidification with cold 1N HCl followed by extraction with $CH_2Cl_2$ regenerated the N-Boc carboxylic acid 26b (1.8 g, 7.11 mmol out of a theoretical 8.51 mmol, 84% yield). $^1$H NMR (DMSO-$d_6$): 7.26 (bs, 1H), 6.66 (bs, 1H), 6.13 (m, 2H), 3.59 (t, 1H, J=6.9 Hz), 2.80 (s, 1H), 2.54 (s, 1H), 2.31 (d, 1H, J=8.1 Hz), 2.00 (d, 1H, J=8.7 Hz), 1.36 (s, 9H), 1.30 (d, 1H, J=8.1 Hz); LCMS: MS (m/z): 254 (MH$^+$); $[\alpha]_D$ −76.78° (c 1.0, MeOH).

6.3.2 Preparation of Stereoisomerically Pure Mono SNAr Product

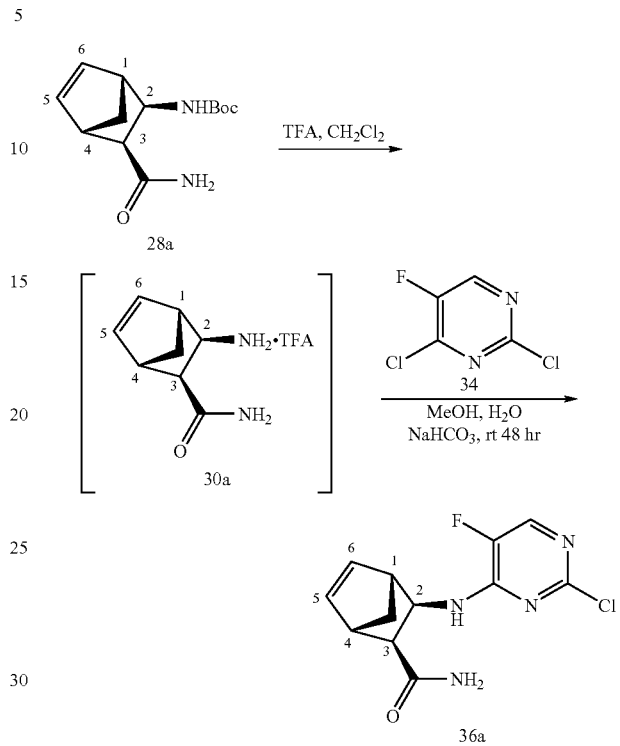

Procedure: A round bottom flask equipped with $N_2$ inlet and a magnetic stirring bar was charged with enantiomerically pure N-BOC carboxyamide 28a (2.00 g, 7.93 mmol) and then treated with 20% of TFA in $CH_2Cl_2$ at room temperature for 2 hours. The reaction progress was monitored by TLC. The resulting solution was concentrated under a reduced pressure. The trace of TFA was removed under high vacuum for several hours to afford the enantiomerically pure intermediate, TFA salt 30a in quantitative yield. $^1$H NMR (DMSO-$d_6$): 8.10 (bs, 2H), 7.92 (s, 1H), 7.25 (s, 1H), 6.29 (m, 1H), 6.18 (m, 1H), 4.38 (bs, 1H), 3.06 (d, 1H, J=7.2 Hz), 2.97 (s, 1H), 2.87 (s, 1H), 2.43 (d, 1H, J=7.5 Hz), 2.10 (d, 1H, J=6 Hz), 1.36 (d, 1H, J=8.7 Hz); LCMS: MS (m/z): 152 (MH$^+$).

The resulting TFA salt 30a was treated with 2,4-dichloro-5-fluoropyrimidine 34 (1.58 g, 9.51 mmol) in MeOH:$H_2O$ (20:10 mL) in the presence of $NaHCO_3$ (1.33 g, 15.84 mmol) at room temperature for 48 hours. The reaction mixture was diluted with $H_2O$ (25 mL), saturated with NaCl and extracted with EtOAc (3×50 mL). Upon drying over anhydrous $Na_2SO_4$ the solvent was evaporated and the residue was chromatographed (silica gel, $CH_2Cl_2$ then 2-4% 2N $NH_3$/MeOH in $CH_2Cl_2$) to afford 2.02 g (91%) of desired mono-SNAr product 36a $^1$H NMR (DMSO-$d_6$): 8.25 (d, 1H, J=7.2 Hz), 8.07 (d, 1H, J=3.3 Hz), 7.71 (s, 1H), 7.19 (s, 1H), 6.29 (m, 2H), 3.99 (t, 1H, J=7.8 Hz), 2.85 (s, 1H), 2.75 (s, 1H), 2.49 (d, 1H, J=0.9 Hz), 2.11 (d, 1H, J=8.7 Hz), 1.39 (d, 1H, J=8.7 Hz); LCMS: purity: 95%, MS (m/z): 283 (MH$^+$). The enantiomeric purity was greater than 99% as determined by chiral HPLC; $[\alpha]_D$ + 61.10° (c 1.0, MeOH).

6.3.3 Preparation of Stereoisomerically Pure (1R,2R, 3S,4S)-N4-(3-Aminocarbonyl bicyclo[2.2.1]hept-5-en-2-yl)-5-fluoro-N-2-[3-methyl-4-(4-methylpiperazin-1-yl)phenyl]-2,4-pyrimidinediamine

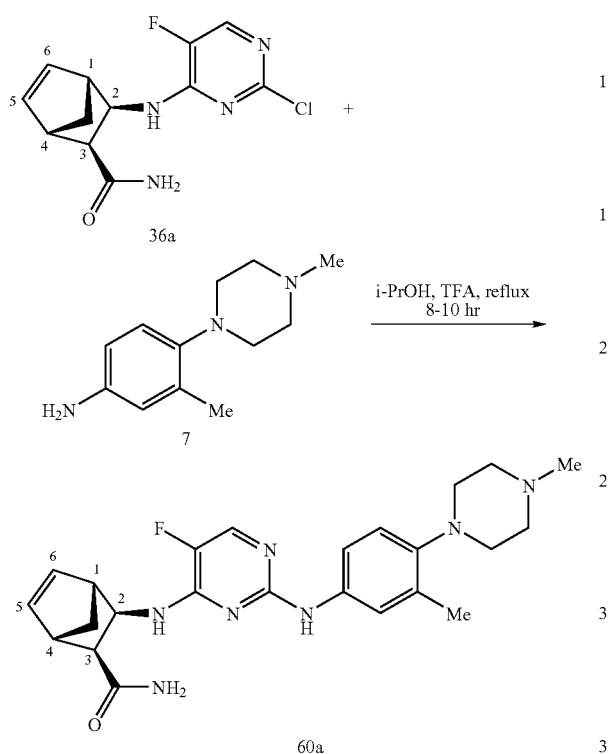

Procedure: A dry reaction flask equipped with a stirring bar, relflux condenser and an N₂ inliet was charged with enantiomerically pure mono-SNAr product 36a (2.25 g, 8 mmol), aniline 7 (1.80 g, 8.8 mmol), TFA (1.12 mL) and isopropanol (18 mL) and the resulting reaction mixture was stirred at reflux temperature for 8-10 hours. After cooling the reaction mixture to room temperature, ethyl acetate (20 mL) was added. The solid obtained was filtered and washed with ethyl acetate (2×5 mL) to afford compound 60a in the form of acidic salt. The resulting solid was then taken into water and the aqueous mixture adjusted to pH 9 with aqueous NaHCO₃, which caused precipitation of a solid. The solid was filtered from the mixture, washed with water and dried to give 3.3 g (93%) of 2,4-pyrimidinediamine derivative 60a. ¹H NMR (DMSO-d₆): 8.85 (s, 1H), 7.83 (d, 1H, J=2.7 Hz), 7.68 (s, 1H), 7.47 (s, 2H), 7.36 (d, 1H, J=7.8 Hz), 7.18 (s, 1H), 6.89 (d, 1H, J=8.7 Hz), 6.32 (m, 1H), 6.25 (m, 1H), 4.11 (t, 1H, J=7.8 Hz), 3.32 (s, 3H), 2.86 (s, 1H), 2.76 (m, 4H), 2.49 (m, 4H), 2.46 (m, 2H), 2.21 (s, 3H), 2.11 (d, 1H, J=8.4 Hz), 1.39 (d, 1H, J=9 Hz); LCMS: purity: 100%, MS (m/z): 452 (M⁺); >99% ee as determined by chiral HPLC; $[\alpha]_D^{RT}$+101.2° (c 1.0, MeOH).

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated into the application by reference for all purposes.

What is claimed is:

1. A method for generating a stereoisomerically pure N-protected β-lactam from a mixture of diastereomers, comprising contacting an N-protected β-lactam mixture comprising enantiomers according to structural formulae (1) and (2):

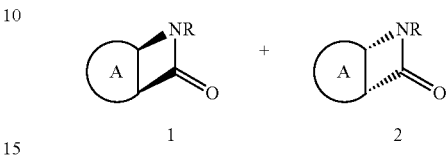

wherein:
A represents a saturated or unsaturated, monocyclic, polycyclic or bridged polycyclic ring; and
R is a carbamate or thiocarbamate protecting group,
with a lipase from *Candida antarctica* under conditions in which the lipase selectively cleaves enantiomer 2, thereby yielding a mixture of reaction products according to structural formulae 1 and 4:

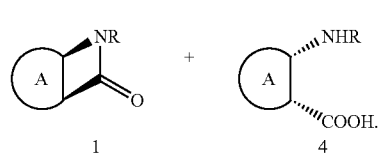

2. The method of claim 1, wherein the carbamate protecting group is of the formula —C(O)OR¹, where R¹ is selected from unsubstituted or substituted alkyl, unsubstituted or substituted (C6-C20) aryl and substituted or unsubstituted (C7-C26) arylalkyl.

3. The method of claim 2, wherein R¹ is selected from t-butyl and benzyl.

4. The method of claim 1, wherein A is selected from bicycloheptenyl, bicycloheptyl, cycloheptyl, cycloheptenyl, cyclohexyl, cyclohexenyl, cyclopentyl, cyclopentenyl, cyclopropyl, and cyclobutyl.

5. The method of claim 1, wherein the lipase is a type B lipase.

6. The method of claim 1, wherein the lipase is bound to a resin.

7. The method of claim 1, wherein a catalytic amount of the lipase is used.

8. The method of claim 1, wherein the contacting is carried out at a temperature in the range of about 0-80° C.

9. The method of claim 8, wherein the temperature in the range of about 20-60° C.

10. The method of claim 1, wherein the contacting is carried out in a solvent selected from diisopropyl ether, tetrahydrofuran, butanol, toluene, hexanes, acetonitrile, and mixtures thereof.

11. The method of claim 10, wherein the solvent has a water content in the range about of 0.1 to 1.0 wt %.

12. The method of claim 1, which further comprises the step of isolating compound 1 from compound 4.

13. The method of claim 12, wherein the isolation is carried out by creating a base addition salt of compound 4 and removing said base addition salt via aqueous extraction of a mixture of an organic solution of compound 1 and said base addition salt.

* * * * *